United States Patent [19]

Effland et al.

[11] Patent Number: 5,055,476
[45] Date of Patent: Oct. 8, 1991

[54] 3-(1,2-BENZISOXAZOL-3-YL)-4-PYRIDINAMINES AND DERIVATIVES

[75] Inventors: Richard C. Effland; Joseph T. Klein, both of Bridgewater, N.J.

[73] Assignee: Hoechst-Roussel Pharmaceuticals Incorporated, Somerville, N.J.

[21] Appl. No.: 566,932

[22] Filed: Aug. 13, 1990

[51] Int. Cl.$^5$ .................... C07D 413/04; A61K 31/44
[52] U.S. Cl. ..................................... 514/338; 546/270
[58] Field of Search ........................ 546/270; 514/338

[56] References Cited

PUBLICATIONS

Gill et al., CA 102:149219k.

Primary Examiner—Jane T. Fan
Attorney, Agent, or Firm—Elliott Korsen

[57] ABSTRACT

This invention relates to 3-(1,2-benzisoxazol-3-yl)-4-pyridinamines of the formula

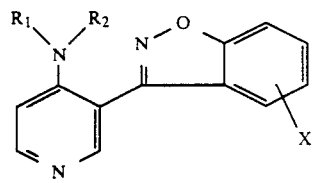

where $R_1$ is hydrogen, loweralkyl, arylalkyl or acyl; $R_2$ is hydrogen, loweralkyl or arylalkyl, X is hydrogen, halogen, nitro or amino; or the pharmaceutically acceptable addition salts thereof, and where applicable, the geometric and optical isomers and racemic mixtures thereof. The compounds of this invention are useful as analgesics, for alleviating various memory dysfunctions characterized by a decreased cholinergic function, as cognition enhancers in the treatment of senile dementia such as Alzheimer's disease and as topical antiinflammatory agents for the treatment of various dermatoses.

12 Claims, No Drawings

3-(1,2-BENZISOXAZOL-3-YL)-4-PYRIDINAMINES AND DERIVATIVES

This invention relates to 3-(1,2-benzisoxazol-3-yl)-4-pyridinamines of the formula

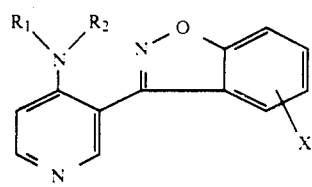

(I)

where $R_1$ is hydrogen, loweralkyl, arylalkyl or acyl; $R_2$ is hydrogen, loweralkyl or arylalkyl; X is hydrogen, halogen, nitro or amino; or the pharmaceutically acceptable addition salts thereof, and where applicable, the geometric and optical isomers and racemic mixtures thereof. The compounds of this invention are useful as analgesics, for alleviating various memory dysfunctions characterized by a decreased cholinergic function, as cognition enhancers in the treatment of senile dementia such as Alzheimer's disease and as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Throughout the specification and appended claims, a given chemical formula or name shall encompass all stereo, optical and geometrical isomers thereof and racemic mixtures where such isomers and mixtures exist.

Unless otherwise stated or indicated, the following definitions shall apply throughout the specification and the appended claims.

The term "loweralkyl" refers to a straight or branched chain hydrocarbon of 1 to 6 carbon atoms, containing no unsaturation, e.g., methyl, ethyl, propyl, isopropyl, 2-butyl, neopentyl, n-hexyl, etc.; the term "arylalkyl" refers to a monovalent substituent which consists of an "aryl" group, e.g., phenyl, o-tolyl, m-methoxyphenyl, etc., as defined by the formula

where Z is defined below, and n is an integer of 1 to 3, linked through an alkylene group having a free valence bond from a carbon of the alkylene group, and having a formula

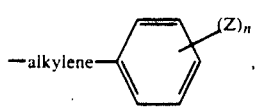

where Z is hydrogen, halogen, loweralkyl, loweralkoxy, trifluoromethyl, nitro and amino; the term "alkylene" refers to a bivalent radical of the lower branched or unbranched alkyl group it is derived from having valence bonds from two terminal carbons thereof, e.g., methylene ($—CH_2—$), ethylene ($—CH_2CH_2—$), propylene ($—CH_2CH_2CH_2—$), isopropylene

($CH_3CHCH_2—$), etc.; the term "acyl" refers to a substituent having the formula loweralkyl

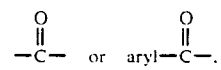

e.g., acetyl, benzoyl, etc., and the term "halogen" refers to a member of the halogen family consisting of fluorine, chlorine, bromine and iodine.

The compounds of this invention are prepared in the following manner. The substituents $R_1$, $R_2$ and X are as defined above unless indicated otherwise.

An oxime of the formula

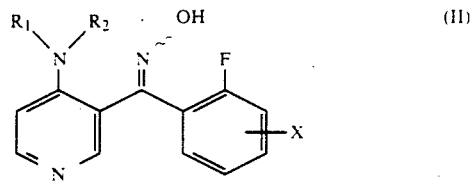

(II)

is cyclized in the presence of a base to afford Compound I. This reaction typically takes place in the presence of a strong base such as sodium hydroxide, potassium hydroxide, potassium t-butoxide, etc. in a loweralkanol solvent such as methanol, ethanol, etc., at a temperature of about 0° to 100° C. (or to reflux) for 1 to 24 hours.

Compound II is prepared by reacting compound III of the formula

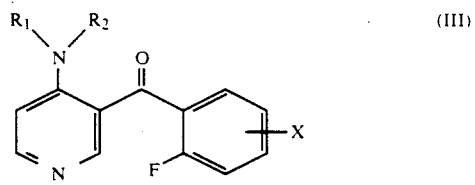

(III)

with hydroxylamine hydrochloride in a suitable solvent such as pyridine or ethanol in the presence of a suitable base, such as sodium acetate at a temperature of 25° C. to reflux.

Compound III is prepared from Compound IV of the formula

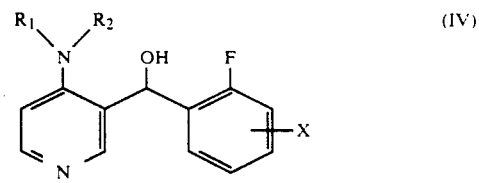

(IV)

by oxidation with pyridinium dichromate or other suitable agents in a suitable solvent such as dimethylformamide.

Compound IV can be prepared in the following manner. 2,2-dimethyl-N-(4-pyridinyl)propanamide of the formula

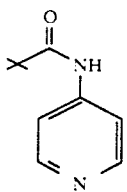

is allowed to react with n-butyllithium and the resultant dianion is allowed to react with ortho-fluorobenzaldehyde of the formula

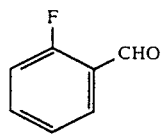

to afford Compound IV. Typically, the first reaction is conducted in a suitable solvent such as tetrahydrofuran at a temperature of about −78° to 25°. The second reaction is also conducted in a suitable solvent such as tetrahydrofuran.

The compounds of the present invention are useful as analgesic agents. This utility is demonstrated in the phenyl-para-quinone writhing assay in mice, a standard assay for analgesia [Proc. Soc. Exptl. Biol. Med., 95, 729 (1957)]. The analgesic effect of compounds of the invention, expressed as % inhibition of writhing, is presented in Table 1.

TABLE 1

| Compound | Dose mg/kg of body wt. s.c. | % Inhibition of Writhing |
|---|---|---|
| 3-(1,2-Benzisoxazol-3-yl)-4-pyridinamine maleate | 20 | 40 |
| Propoxyphene (standard) | 3.9 | 50 |

The analgesic relief of pain is achieved when the compounds of the invention are administered to a subject requiring such treatment at an effective oral, parenteral or intraveneous dose of from 0.1 to 25 mg/kg of body weight per day, a particularly effective amount is about 5 mg/kg of body weight per day. It is to be understood that for any particular subject, specific dosage regimens should be adjusted according to the individual need and the professional judgment of the person administering or supervising the administration of the aforesaid compound. It is to be further understood that the dosages set forth herein are exemplary only and that they do not to any extent limit the degree or practice of the invention.

The compounds of the present invention can also be used for the treatment of various memory dysfunctions characterized by decreased cholinergic function such as Alzheimer's disease. This utility is demonstrated in the Dark Avoidance Assay.

DARK AVOIDANCE ASSAY

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chambers, the animal re-enters the dark compartment shortly after being placed in the test chamber 24 hours later. The effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of some of the compounds of this invention and a reference compound are presented in Table 2.

TABLE 2

| Compound | Dose mg/kg s.c. | % of Animals with Scopolamine Induced Memory Deficit Reversal |
|---|---|---|
| N-[3-(1,2-Benzisoxazol-3-yl)-4-pyridinyl]-2,2-dimethylpropanamide | 3.0 | 20 |
| 3-(1,2-Benzisoxazol-3-yl)-4-pyridinamine maleate | 10.0 | 33 |
| | 1.0 | 21 |
| Physostigmine (reference) | 0.31 | 20 |

The compounds of this invention are also useful as topical antiinflammatory agents for the treatment of various dermatoses as mentioned earlier. The dermatological activity of the compounds of this invention was ascertained with reference to the following methods.

DERMATOLOGICAL TEST METHODS

TPA-Induced Ear Edema (TPAEE)

The purpose of this assay was to determine the ability of a topically-applied compound to prevent ear edema induced by topical application of TPA (phorbol 12-myristate acetate). Female Swiss Webster mice topically received TPA (10 μg/ear) on the right ear and vehicle on the left ear. The test compound (10 μg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50}=47$ μg/ear). See Young, J. M. et al., J. Invest. Dermatol., 80 (1983), pp. 48–52.

Dermatological activities for the compounds of this invention are presented in Table 3.

TABLE 3

| Compound | TPAEE (10 μg) |
|---|---|
| N-[3-(1,2-Benzisoxazol-3-yl)-4-pyridinyl]-2,2-dimethylpropanamide | −23% |
| 3-(1,2-Benzisoxazol-3-yl)-4-pyridinamine maleate | −29% |

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™ corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:

N-[3-(1,2-Benzisoxazol-3-yl)-4-pyridinyl]-N-methyl-2,2-dimethylpropanamide;

3-(1,2-Benzisoxazol-3-yl)-N-methyl-4-pyridinamine;

3-(1,2-Benzisoxazol-3-yl)-N-phenylmethyl-4-pyridinamine;

3-(5-Nitro-1,2-benzisoxazol-3-yl)-4-pyridinamine;

3-(5-Amino-1,2-benzisoxazol-3-yl)-4-pyridinamine; and 3-(6-Fluoro-1,2-benzisoxazol-3-yl)-4-pyridinamine.

The following examples are given for illustrative purposes and are not to be construed as limiting the invention disclosed herein.

EXAMPLE 1 a. α-(2-Fluorophenyl)-4-aminopyridine-3-methanol hydrochloride

A solution of α-[4-(2,2-dimethylpropionamido)-3-pyridinyl]-α-(2-fluorophenyl)-methanol (18 g) in 200 mL methanol and 20 mL 10% aqueous sodium hydroxide was stirred at 75°–80° for two hours then was cooled, evaporated, stirred with water and extracted with ethyl acetate-ether. The organic extract was washed with water and saturated sodium chloride, then dried (anhy. MgSO$_4$), filtered and evaporated to 13 g of an oil. This was purified by flash chromatography (silica, 20% methanol in dichloromethane) to yield 11.5 g of the product as a solid, m.p. 60°–65° C. Three grams were converted to the hydrochloride salt in methanol-ether to yield 2.8 g of a solid, m.p. 210°–213° C. This was recrystallized from methanol-ether to yield 2.2 g of α-(2-fluorophenyl)-4-aminopyridine-3-methanol hydrochloride, m.p. 215°–216° C.

Analysis: Calculated for C$_{12}$H$_{12}$ClFN$_2$O: 56.59% C; 4.75% H; 11.00% N. Found: 56.60% C; 4.75% H; 10.94% N.

b. (4-Amino-3-pyridinyl)-(2-fluorophenyl)-methanone oxime

A solution of (4-amino-3-pyridinyl)-(2-fluorophenyl)-methanone (19 g) and hydroxylamine hydrochloride (31 g) in 125 mL pyridine stirred at reflux for two hours then was cooled and evaporated. The residue was stirred with water, basified with sodium bicarbonate and extracted with ethyl acetate-ether. The organic extract was washed with water and saturated sodium chloride, was dried (anhy. MgSO$_4$), filtered and evaporated to 25 g of an oil. This oil was eluted with 10% methanol in dichloromethane through silica via flash chromatography to yield 14.6 g of a solid, m.p. 170°–180° C. Three grams were recrystallized from acetonitrile to yield 1.7 g of (4-amino-3-pyridinyl)-(2-fluorophenyl)-methanone oxime, as a solid, m.p. 212°–214° C.

Analysis: Calculated for C$_{12}$H$_{10}$FN$_3$O: 62.33% C; 4.36% H; 18.18% N. Found: 62.11% C; 4.41% H; 17.99% N.

c. N-[3-(1,2-Benzisoxazol-3-yl)-4-pyridinyl]-2,2-dimethylpropanamide

A solution of [4-(2,2-dimethylpropionamido)-3-pyridinyl]-2-fluorophenyl-methanone oxime (2.3 g) in 20 mL methanol and 2 mL 10% aqueous sodium hydroxide was stirred at reflux for two hours then cooled, stirred with water and extracted with dichloromethane. The dried (anhydrous magnesium sulfate) organic layer was filtered and evaporated to 2.4 g of a solid. This was combined with 1.5 g of product obtained from an earlier run and was eluted through silica with 5% ethyl acetate in dichloromethane (DCM) via flash column chromatography to yield 2.5 g of a solid, mp 133°–134° C. The solid was recrystallized from methanol to yield 2.3 g of N-[3-(1,2-benzisoxazol-3-yl)-4-pyridinyl]-2,2-dimethylpropanamide, mp 137°–138° C.

Analysis: Calculated or $C_{17}H_{17}N_3O_2$: 69.13% C; 5.80% H; 14.23% N. Found: 69.11% C; 5.82% H; 14.19% N.

EXAMPLE 2

3-(1,2-Benzisoxazol-3-yl)-4-pyridinamine maleate

A solution of [4-(2,2-dimethylpropionamido)-3-pyridinyl]-2-fluorophenyl-methanone oxime (5.2 g) in 60 mL methanol and 10 mL 10% aqueous sodium hydroxide was stirred at reflux for four hours then cooled, stirred with water and extracted with DCM. The dried (anhydrous magnesium sulfate) organic layer was filtered and evaporated to 3.7 g of an oil. This oil was eluted through silica with 20% ethyl acetate in DCM, then ethyl acetate, via flash column chromatography to yield 2.2 g of the product as a solid, mp 146°–148° C. This solid was converted to the maleate salt in methanol then was recrystallized from methanol to yield 3.3 g of 3-(1,2-benzisoxazol-3-yl)-4-pyridinamine maleate, (dec) 188°–190° C.

Analysis: Calculated for $C_{16}H_{13}N_3O_5$: 58.71% C; 4.00% H; 12.84% N. Found: 58.66% C; 3.99% H; 12.84% N.

We claim:

1. A compound of the formula

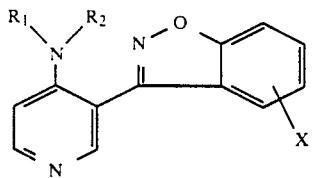

where $R_1$ is hydrogen, loweralkyl, arylalkyl or acyl; $R_2$ is hydrogen, loweralkyl or arylalkyl, the term aryl in each occurrence signifying a phenyl group optionally substituted as defined by the formula

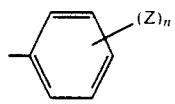

where Z is hydrogen, halogen, loweralkyl, loweralkoxy, trifluoromethyl, nitro and amino, and n is an integer of 1 to 3; the term acyl in each occurrence signifying a substituent having the formula

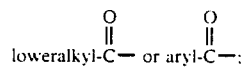

or a pharmaceutically acceptable addition salt thereof, or where applicable a geometric or optical isomer or a racemic mixture thereof.

2. The compound as defined in claim 1 wherein $R_1$ is acyl.

3. The compound as defined in claim 2 which is N-[3-(1,2-benzisoxazol-3-yl)-4-pyridinyl]-2,2-dimethylpropanamide.

4. The compound as defined in claim 1 wherein $R_1$ is hydrogen.

5. The compound as defined in claim 4 which is 3-(1,2-benzisoxazol-3-yl)-4-pyridinamine.

6. The compound as defined in claim 5 where the salt is the maleate.

7. A pharmaceutical composition which comprises a compound as defined in claim 1 present in an amount effective for treating pain and a suitable carrier therefor.

8. A pharmaceutical composition for enhancing memory which comprises an effective memory enhancing amount of a compound as defined in claim 1 and a suitable carrier therefor.

9. A dermatological composition which comprises a compound as defined in claim 1 present in an amount effective for treating a skin disorder and a suitable carrier therefor.

10. A method of treating a patient in need of relief from pain which comprises administering to the patient a pain alleviating effective amount of a compound as defined in claim 1.

11. A method of treating a patient in need of memory enhancement which comprises administering to a patient a memory enhancing effective amount of a compound as defined in claim 1.

12. A method of treating a patient in need of relief from a skin disorder which comprises administering to such a patient an effective amount of a compound as defined in claim 1.

* * * * *